(12) United States Patent
Barbera Betancourt et al.

(10) Patent No.: US 8,410,057 B2
(45) Date of Patent: *Apr. 2, 2013

(54) METHOD OF INDUCING T CELL APOPTOSIS BY ADMINISTERING ALTERED PEPTIDE LIGAND

(75) Inventors: Ariana Barbera Betancourt, Ciudad de la Habana (CU); Maria del Carmen Dominguez Horta, Ciudad de la Habana (CU); Norailys Lorenzo Perez, Ciudad de la Habana (CU); Gabriel Ramon Padron Palomares, Ciudad de La Hababa (CU); Viviana Falcon Cama, Ciudad de La Habana (CU); Ivon Menendez Valdes, Ciudad de la Habana (CU)

(73) Assignee: Centro de Ingenieria Genetica y Biotecnologia, Ciudad de la Habana (CU)

( * ) Notice: Subject to any disclaimer, the term of this patent is extended or adjusted under 35 U.S.C. 154(b) by 0 days.

This patent is subject to a terminal disclaimer.

(21) Appl. No.: 13/142,471

(22) PCT Filed: Dec. 29, 2009

(86) PCT No.: PCT/CU2009/000009
§ 371 (c)(1),
(2), (4) Date: Sep. 26, 2011

(87) PCT Pub. No.: WO2010/075824
PCT Pub. Date: Jul. 8, 2010

(65) Prior Publication Data
US 2012/0035106 A1    Feb. 9, 2012

(30) Foreign Application Priority Data

Dec. 29, 2008  (CU) .................................. 2008-0254

(51) Int. Cl.
| | | |
|---|---|---|
| *A61K 38/00* | (2006.01) | |
| *A61K 38/16* | (2006.01) | |
| *A61P 43/00* | (2006.01) | |
| *A61P 3/10* | (2006.01) | |
| *A61P 7/12* | (2006.01) | |
| *A61P 1/04* | (2006.01) | |

(52) U.S. Cl. ....... 514/18.9; 514/7.3; 514/13.2; 514/21.3
(58) Field of Classification Search .................. None
See application file for complete search history.

(56) References Cited

U.S. PATENT DOCUMENTS

2010/0144642 A1* 6/2010 Dominguez Horta et al. . 514/13

* cited by examiner

Primary Examiner — Robert Landsman
(74) Attorney, Agent, or Firm — Hoffmann & Baron, LLP (57) ABSTRACT

The present invention is related with the field of the medicine, particularly with the use of an APL peptide or its analogues derived from the human heat shock protein of 60 kDa, for the manufacture of a pharmaceutical composition for the treatment of Crohn's disease, ulcerative colitis and diabetes mellitus type 1. This peptide is biodistributed into the gastrointestinal tract and also promotes the induction of apoptosis in activated intestinal lamina propria and peripheral blood T cells of patients with Crohn's disease. Furthermore, this peptide induces apoptosis in mononuclear cells of patients with diabetes mellitus type 1.

5 Claims, 4 Drawing Sheets

SEQUENCE LISTING

```
<160> NUMBER OF SEQ ID NOS: 1

<210> SEQ ID NO 1
<211> LENGTH: 27
<212> TYPE: PRT
<213> ORGANISM: Artificial Sequence
<220> FEATURE:
<223> OTHER INFORMATION: Description of the Artificial Sequence: APL
      Peptide

<400> SEQUENCE: 1

Ser Ile Asp Leu Lys Asp Lys Tyr Lys Asn Ile Gly Ala Lys Leu Val
 1               5                  10                  15

Gln Leu Val Ala Asn Asn Thr Asn Glu Glu Ala
            20                  25
```

METHOD OF INDUCING T CELL APOPTOSIS BY ADMINISTERING ALTERED PEPTIDE LIGAND

CLAIM OF PRIORITY

This application is the U.S. National Phase of, and Applicants claim priority from, International Application Number PCT/CU2009/000009 filed 29 Dec. 2009 and Cuban Patent Application No. CU 2008-0254 filed 29 Dec. 2008, which are incorporated herein by reference.

INCORPORATION OF SEQUENCE LISTING

Incorporated herein by reference in its entirety is the Sequence Listing for the above-identified Application. The Sequence Listing is disclosed on a computer-readable ASCII text file titled "SequenceListing976_77PCTUS.txt", created on Jun. 27, 2011. The sequence.txt file is 808 bytes size.

FIELD OF THE INVENTION

The present invention is related with the field of the medicine, particularly with the use of an APL peptide (Altered Peptide Ligand, abbreviated APL) or its analogues for the treatment of inflammatory bowel disease (as Crohn's disease and ulcerative colitis) and diabetes mellitus type 1.

PREVIOUS ART

Inflammatory bowel diseases, as Crohn's disease and ulcerative colitis, result from the activation of intestinal lamina propria T cells with potent effector functions toward the commensal flora. However, the exact mechanism which lead to the chronic activation of these lymphocytes remain uncertain (Balfour R (2006) Mechanism of Disease: pathogenesis of Crohn's disease and ulcerative colitis. Nature clinical practice. Gastroenterology and Hepatology 3 (7): 390-407).

Approximately $2 \times 10^4$ bacteria reside in the gastrointestinal tract, and this immunological pressure represents an extraordinary challenge to the immune system, which has to perform a balancing act between appropriate responsiveness to pathogenic organisms and tolerance for harmless organisms. The mucosal immune system has several mechanisms to avoid an unnecessary and uncontrolled inflammatory response, such as the decrease of activated T cells by apoptosis (Peppelenbosch M P and van Deventer S J H (2004) T cell apoptosis and inflammatory bowel disease. Gut 53: 1556-1558).

The immune system under normal conditions quickly clear infections of invasive enteric bacteria, downregulate innate immune responses and heal the injured mucosa without stimulating effector T-cell responses. By contrast, the immune system of genetically susceptible hosts is unable to mount an appropriate innate response and/or generate tolerogenic immune response to commensal microbial agents, subsequently activate pathogenic T-cell responses to commensal bacteria and proceed to chronic intestinal inflammation (Podolsky D K (2002) Inflammatory bowel disease. N Engl J Med 347: 417-29).

Thus, inflammatory bowel disease results from the failure to the mechanisms that appropriately controls the inflammatory processes initiated by an environmental trigger, such as an acute intestinal infection. Resistance to T-cells apoptosis, lack of response to downregulatory signals and continuous exposure to luminal antigens and adjuvants help sustain this inflammatory response (Mudter J and Neurath M F (2007) Apoptosis of T cells and the control of inflammatory bowel disease: therapeutic implications. Gut 56:293-303).

Crohn's disease is characterized by an enhanced recruitment of macrophages, neutrophils and T cells into the intestine, which lead to an increment in the expression of costimulatory and adhesion molecules, as well as proinflammatory cytokines related with TH1 (T cell helper 1, abbreviated TH1), for example: interleukin (IL)-6 (IL-6) and tumor necrosis factor-alpha (TNF-α) and TH17 cellular responses (T cell helper 17, abbreviated TH17) as: IL-12, IL-23 and IL-27 (Balfour R (2006) Mechanism of Disease: pathogenesis of Crohn's disease and ulcerative colitis. Nature clinical practice. Gastroenterology and Hepatology 3 (7): 390-407).

The number of inflammatory cells in the intestine is determined by cellular recruitment, proliferation and death by necrosis or apoptosis. Lamina propria T cells from normal intestinal mucosa are susceptible to activation-induced cell death (through Fas/FasL system), which is able to control the proliferation of lymphocytes (Bu P et al. (2001) Apoptosis: one of the mechanisms that maintains unresponsiveness of the intestinal mucosal immune system. J Immunol 166: 6399-6403). However, data indicate that lamina propria T cells in Crohn's disease patients are resistant to apoptosis, which could lead to an expanded population of activated effector TH1 cells that might contribute to disease perpetuation and chronic inflammation (Boirivant M et al. (1999) Lamina propria T cells in Crohn's disease and other gastrointestinal inflammation show defective CD2 pathroute-induced apoptosis. Gastroenterology 116: 557-565).

The apoptosis defect in mucosal T cells in Crohn's disease patients has been attributed to an imbalance between the proportions of anti-apoptotic molecules like Bcl-2 and pro-apoptotic molecules as Bax, which prolongs the survival of these cells and lead to the resistance of apoptotic signals (Ina K et al. (1999) Resistance of Crohn's disease T cells of multiple apoptotic signals is associated with Bcl2/Bax mucosal imbalance. J Immunol 163:1081-90; Itoh J et al. (2001) Decreased Bax expression by mucosal T cells favours resistance to apoptosis in Crohn's disease. Gut 49: 35-41). On the other hand, Sturm and colleagues studied the cell cycle properties of mucosal T cells from patients with Crohn's disease, ulcerative colitis and healthy controls. They showed that mucosal T cells in Crohn's disease patients have an impressive capacity for cellular expansion because faster cycle compared with mucosal cells of patients with ulcerative colitis or healthy controls, probably as a result of a defect in activation dependent apoptosis. These could explain why the mucosa of Crohn's disease patients contains an excess of T cells indicating a state of hyperreactivity and also the loss of the tolerance to the commensal bacteria (Sturm A et al. (2004) Divergent cell cycle kinetics underlies the distinct functional capacity of mucosal T cells in Crohn's disease and ulcerative colitis. Gut 53:1624-1631).

These experimental evidences sustain the fact that Crohn's disease is a disorder in which cellular proliferation events overcome death by apoptosis leading to the accumulation of reactive T cells in the inflammation site, which could be an important factor in the pathogenesis of the disease. In this sense, the most powerful biologicals used in the treatment of this disease seem to be those inducing apoptosis in monocytes and T cells, for example: antibodies to TNFα, IL-12 or IL-6 receptor (Lügering et al. (2001) Infliximab induces apoptosis in monocytes from patients with chronic Crohn's disease by using it activates to caspase dependent pathroute. Gastroenterology 121: 1145-57), (Stallmach et al. (2004) An interleukin 12 p40-IgG2b coalition protein abrogates T cell mediated inflammation: anti-inflammatory activity in Crohn's disease and experimental colitis in alive. Gut 53: 339-45), (Atreya R et al. (2000) Blockade of interleukin 6 trans-signaling suppresses T-cell resistance against apoptosis in chronic intestinal inflammation: evidence in Crohn's disease and experimental colitis in alive. Nat Med 6: 583-588). In particular, antibodies to TNFα are an important option to induce long remission in steroid refractory patients with Crohn's disease.

Infliximab is a chimeric monoclonal antibody (AcM) that contains the murine variable region and the constant region of a human immunoglobuline G1 (IgG1) molecule that binds to and neutralizes the effects of both free and bound TNFα with a huge affinity and specificity (Knight D M K et al. (1993) Construction and initial characterization of a mouse-human chimeric anti-TNF antibody. Mol Immunol 30: 1443-1453).

Etanercept is a recombinant protein that contains two monomeric chains of the soluble portion of the human tumor necrosis factor receptor 2 (TNFR2), fused to the Fc portion of a human IgG1 (Mohler K M et al. (1993) Soluble tumor necrosis factor (TNF) receptors are effective therapeutic agents in lethal endotoxemia and function simultaneously as both TNF carriers and TNF antagonists. J Immunol 151: 1548-1561). This molecule has been successfully used in the treatment of other inflammatory diseases as Rheumatoid Arthritis (RA) (Moreland L W et al. (1999) Etanercept therapy in rheumatoid arthritis. To randomized, controlled trial. Ann Intern Med 130: 478-486). However, etanercept contrary to infliximab, does not offer clinical benefits in Crohn's disease. Van den Brande and colleagues demonstrated that the difference in the effectiveness of both drugs, in the treatment of Crohn's disease, is due to the capacity of infliximab to induce apoptosis of monocytes and activated lamina propria T cells (Van de Brande J M H et al. (2003) Infliximab but not Etanercept induces apoptosis in lamina propria T-Lymphocytes from patients with Crohn's disease. Gastroenterology 124: 1774-1785). Etanercept does not induce cell apoptosis, as infliximab, which is effective in Crohn's disease due to its pro-apoptotic effects as it been suggested.

The clinical results obtained in treated Crohn's disease patients using Infliximab and other drugs that induce T-cell apoptosis have suggested that restoration of the apoptosis in the mucosal T cells compartment may be an important factor for successful treatment of Crohn's disease.

Up to this moment, infliximab is the most successful therapy for the treatment of Crohn's disease patients. This therapy has also been applied with encouraging results in patients with ulcerative colitis. However, the use of this therapy produces a group of adverse reactions, as the increase of the incidence of illnesses in these patients like tuberculosis and mycoplasmosis, due to the widespread immune suppression that takes place (Kooloos W M. (2007) Potential role of pharmacogenetics in anti-TNF treatment of rheumatoid arthritis and Crohn's disease. Drug Discovery Today 12: 125-31). As a consequence, the main challenge at the present time is the development of therapeutic strategies that can eliminate pathogenic cells with specificity, without causing a widespread immune suppression.

With this purpose, antigen-specific strategies have been applied in the last years with the intention of regulating the immune response, not of suppressing it. In this sense, native autoantigenic or APL peptides have been used, administered under such conditions in order to induce peripheral tolerance mechanisms (Prakken B et al. (2004) Epitope-specific immunotheraphy induces immune deviation of proinflammatory T cells in RA. PNAS 12 (101): 4228-33; Ben-David H et al. (2005) Down-regulation of myasthenogenic T cell response by to dual altered peptide ligand via CD4+CD25+-regulated events leading to apoptosis. PNAS 102 (6): 2028-33; Paas-Rozner M et al. (2001) The nature of the active suppression of responses associated with experimental autoimmune myasthenia gravis by a dual altered peptide ligand administered by different routes. PNAS 98 (22): 12642-7).

APLs are analogues of immunogenic peptides with one or several substitutions in the essential positions of contact with the T cell receptor or Major Histocompatibility Complex that interfere or modify the cascade of necessary events for the complete to activation of T cells (Bielekova B and Martin R (2001) Antigen-specific immunomodulation via altered peptide ligands. J Mol Med 79: 552-65). The capacity to experimentally manipulate the intrinsic properties of peptide ligands allows altering the nature, the course and the power of the immune cellular response appropriately. In the international application of patent No. WO 2006/032216, APL peptides derived is from human heat shock protein of 60 kDa (abbreviated Hsp60) are claimed, as well as the use of a pharmaceutical preparation of such peptides for the treatment of RA. Diabetes mellitus type 1, is an autoimmune organ specific disease that is mediated by T cells that destroy the β cells of the pancreas that produce the insulin, leading to a deregulation of the glucose metabolism (Brown L and Eisenbarth G S (1990) Type 1 diabetes: A chronic autoimmune disease of human, mouse, and rat. Annu Rev Immunol 8: 647-79). The clinical symptoms of this disease appear after the immune system has inactivated near the 80-90% of pancreas cells. Current therapy is directed to find a safe, specific and effective method to turn off the autoimmune process before a permanent damage occur in pancreas cells in order to preserve the endogenous production of insulin. The induction of tolerance has been a concept that has extended for the treatment of type 1 diabetes. Irun Cohen and colleagues have protected the use of human Hsp60 peptides for the diagnosis and treatment of this disease (U.S. Pat. No. 6,682,897).

DESCRIPTION OF THE INVENTION

The present invention solves the problem previously mentioned providing a new therapeutic option for the treatment of inflammatory bowel disease (as Crohn's disease and ulcerative colitis) and diabetes mellitus type 1. The essence of the invention is the use of an immune modulator APL peptide or its analogues derived of the human Hsp60 for the production of a pharmaceutical composition for the treatment of inflammatory bowel disease and diabetes mellitus type 1. This peptide, whose sequence is SIDLKDKYKNIGAKLVQL-VANNTNEEA, is identified in the Sequence Listing as Seq ID No. 1.

This peptide promotes the induction of apoptosis of activated intestinal lamina propria and peripheral blood T cells of patients with Crohn's disease, resulting in the inhibition of T-cell clones involved in the pathogenesis of the disease, without causing an unspecific immune suppression as occur with the use of TNFα antibodies.

The use of this immune modulator APL peptide or its analogues, for the treatment of inflammatory bowel disease, is directed to neutralize clones of T cells that contribute to the characteristic inflammatory process of the disease.

The pharmaceutical preparation of the invention is characterized by its high specificity, because of the neutralization of pathogenic activated T cells. This fact contributes markedly to the safety of this preparation, since it minimizes adverse reactions like opportunistic infections causing tuberculosis and mycoplasmosis, which is associated with the widespread immune suppression cause by the use of drugs like infliximab, or the development of neoplasic processes, as lymphomas due to the use of methotrexate.

The use of the previously mentioned immune modulator peptide in the production of a drug for the treatment of inflammatory bowel disease also has the advantage that independently of its administration by parenteral route (intradermal, subcutaneous or intravenous, for example), its active principle is essentially biodistributed into the gastrointestinal tract: stomach, small intestine and colon. Also, the peptide remains in these organs the necessary time to exert its biological mechanisms. As previously described, in bowel disease the uncontrolled activation of effector T cells against the commensal flora takes place in the gastrointestinal tract. The biodistribution of this peptide and the capacity of inducing apoptosis of pathogenic luminal T cells, justifies the rationality of using this APL peptide for the treatment of Crohn's disease and ulcerative colitis. The use of the pharmaceutical preparation of the invention can be extended to other inflammatory diseases characterized by relapses-remission episodes, in which autorreactive T cells also have an important role, as type 1 diabetes.

The APL identified in the Sequence Listing as Seq ID No. 1 is claimed for the use of a pharmaceutical preparation of the peptide for the treatment of RA in the international patent application WO 2006/032216. However, this patent application neither claims nor suggests that this peptide can be used for the treatment of inflammatory bowel disease and diabetes mellitus type 1.

Inflammatory bowel disease is not considered an autoimmune disease, because the immune response against autoantigens is not responsible for the beginning and maintenance of the inflammation, and at least until this moment causally related autoantigens are not known, which is in contrast to autoimmune diseases. The origin of these diseases depends on the presence of the commensal flora and the immune response directed against the commensal organisms. One of the experimental evidences that sustain this fact is that under germ-free conditions experimental IBD disease can not be induced, unless the gut flora is reconstituted (Chandran et al. (2003) Inflammatory bowel disease: dysfunction of GALT and gut bacterial flora (II). Surgeon 1:125-136; Strober et al. (2002) The immunology of mucosal models of inflammation. Annu. Rev. Immunol 20:495-549). Therefore, supposedly, bacterial antigens are supposed to trigger the induction of the disease.

In U.S. Pat. No. 6,682,897, Irun Cohen and colleagues revealed the use of human Hsp60 peptides for the diagnosis and treatment of type 1 diabetes. The sequence identified as Seq ID No. 1 is not included in that patent and also similar biological activity to the peptide of Seq ID No. 1 is not considered. Contrary to these authors, in the present invention we disclose the use of the peptide of Seq ID No. 1, an APL peptide derived from human Hsp60, to induce apoptosis of pathogenic T cells involved in the development of this pathology.

The examples of the present invention showed for the first time the properties of the peptide of Seq ID No. 1, related with its biodistribution into the gastrointestinal tract and its capacity to induce apoptosis of pathogenic clones of T cells that make possible the use of this peptide for the treatment of Crohn's disease, ulcerative colitis and type 1 diabetes. For those skilled in the art, it was not possible to predict the novel use of the peptide claimed in the present invention based on the elements given in the international patent application No. WO 2006/032216.

The peptide of sequence identified as Seq ID No. 1 or its analogues can be produced by the routine methods of peptide synthesis and can be evaluated by the level and the quality of the immune response induced in experiments like those described in the examples that will be presented later on.

In the context of this invention, the analogue term refers to APL peptides that included one or more deviations of the described sequence (Seq ID No.1), but retain the same biological activity that the described peptide. The modification can be a substitution, deletion or insertion of a single amino acid, preferably a substitution. The analogue will include preferably less than 9 modifications, more preferably less than 6 modifications and even more preferably less than 2 modifications of the described peptide.

It is also an object of the invention a pharmaceutical composition for the treatment of inflammatory bowel disease and type 1 diabetes that comprises an APL peptide derived from human Hsp60 identified as Seq ID No. 1 or its analogues. The amounts of peptide in the pharmaceutical compositions of the present invention are those that produce the effective immune response in the host. The effective amount is the quantity administered that causes the induction of T cell apoptosis that significantly diminish the inflammatory signs of Crohn's disease and turn off the inflammatory focuses of the gastrointestinal tract which is characteristic of the course of these disease. In the course of the treatment, the amount of the pharmaceutical composition administered to a patient can vary according to certain factors like: age, sex, general health, as well as the level of immunological response in general.

The present invention is also related to a method of treatment for inflammatory bowel disease (as Crohn's disease and ulcerative colitis) and type 1 diabetes, which includes the administration to a patient of effective amounts of the pharmaceutical compositions that comprise the identified peptide as Seq ID No. 1 or its analogues.

According to this invention, in the course of the treatment of inflammatory bowel disease (as Crohn's disease and ulcerative colitis) and type 1 diabetes, the pharmaceutical composition is administered by parenteral or mucosal route. According to this invention, the pharmaceutical composition is administered by a parenteral route selected from the group that includes the intradermal route, the subcutaneous route, the intramuscular route and the intravenous route. In another embodiment, the pharmaceutical composition is administered by a mucosal route selected from the group that includes the rectal route and the oral route. Due to the nature of these diseases, the APL peptide or its analogues can be part of formulations administered as enema or as pharmaceutical forms appropriated for the administration by oral route.

EXAMPLES

Example 1

Effect of APL Peptide on Viability of Peripheral Blood Mononuclear Cells from Patients with Active Crohn's Disease and Healthy Donors Blood from patients with Crohn's disease and healthy donors was extracted by vein punction and collected in sterile tubes containing an anticoagulant solution (sodium citrate 123 mM, sodium monobasic phosphate 18.5 mM, citric acid 17 mM and glucose 141.5 mM). Blood from each patient was diluted 1:2 in Phosphate Buffered Saline solution 1× (abbreviated PBS1×) and 5 mL of this dilution were added to 3 mL of Ficoll-Paque™ Plus (Amersham, Biosciences AB, Sweden) in centrifugation tubes of 15 mL and centrifuged during 30 min. at 1200 rpm. The ring corresponding to mononuclear cells was extracted. Later on, the cells were washed twice with 15 mL of PBS 1× and after each washing, they were centrifuged at 900 rpm. Finally, the pellet of the cells was suspended in RPMI 1640 containing 10% of bovine fetal serum and supplemented with penicillin (100 U/mL), streptomycin (100 µg/mL), HEPES 25 mM/L and L-glutamine 2 mM (all acquired from Gibco BRL). Cells from diluted cell suspension (1:20 dilution in supplemented RPMI and 1:2 in trypan blue (Boehringer Mannheim, Germany) were counted using a Neubauer counting chamber.

Mononuclear cells were seeded at a density of $10^5$ cells/well in flat bottom 96-well plates (Costar, USA) in a final volume of 100 µL and were treated in triplicate with different concentrations of the APL peptide (Seq ID No. 1): 10, 40 and 160 ug/mL for 72 hours. Untreated cells were used as control of the basal growth.

The effect of the APL peptide on cell viability was determined using the 3-(4,5-dimethyldiazol-2-yl)-2,5 diphenyl Tetrazolium Bromide (MTT, Sigma, USA) method, following the protocol described by suppliers. MTT is reduced by mitochondrial dehydrogenase enzymes found in metabolically active cells into a formazan product that is not soluble in tissue culture medium. The amount of formazan product measured by the absorbance at 562 nm is directly proportional to the number of living cells in culture. After culturing cells at 37° C., in humid atmosphere of $CO_2$ at 5% for 72 hours, 20 uL of MTT (5 mg/mL) was added to each well. Next, plates were incubated during 4 hours in equal culture conditions. Afterwards, 100 uL of 2-butanol solution was added (sodium dodecyl sulphate (SDS) at 20%, 2-butanol at 50% and 5 mL of hydrochloric acid 2N) and each well was homogenized by soft pipeting. Later on, plates were maintained on continuous agitation for 30 minutes at 37° C. in order to dissolve completely the formazan product. Finally, the absorbance at 562 nm was recorded using a 96-well plate reader.

GraphPad Prism Software program was used for statistical analysis. The data were expressed as mean+/−SE. The statistical test used was Kruskal-Wallis, which is a nonparametric test for multiple comparisons. Next, the Dunn test was used to identify the groups whose media statistically differed. A value of $p<0.05$ was considered significant.

Figure 1:
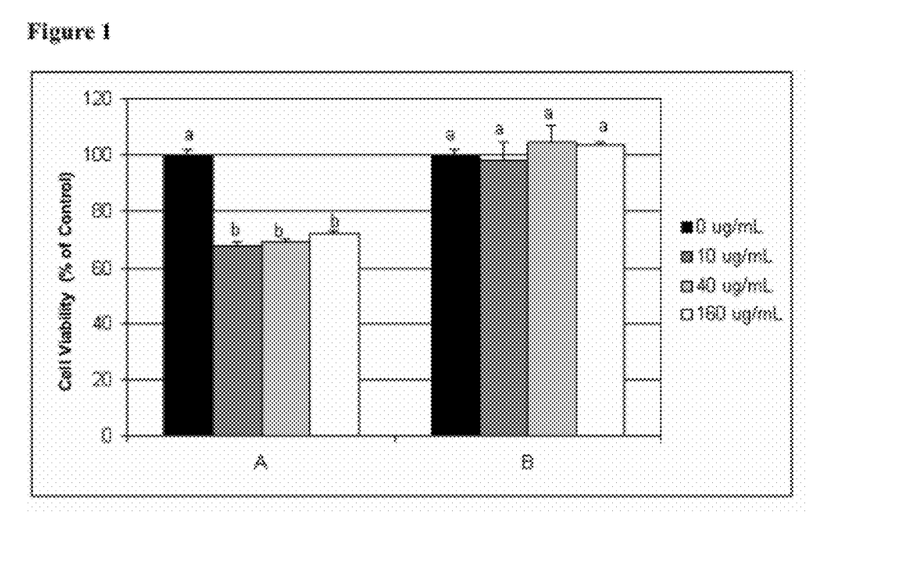
FIGS. 1A-1B. Effect of peptide of Seq ID No. 1 on the viability of peripheral blood mononuclear cells viability from patients with active Crohn's disease (A) and healthy donors (B). Different letters indicate significant statistical differences between the negative control (0 ug/mL) and each one of the doses of the peptide evaluated in this group.

As it is shown in FIG. 1, APL peptide treatment significant reduce the viability of peripheral blood mononuclear cells from patients with active Crohn's disease at all doses of the peptide comparing with untreated cells ($p<0.001$). However, the treatment with this peptide does not affect the viability of mononuclear cells from healthy donors (at none of the doses of APL peptide evaluated in the experiment). This result suggests the specificity of the cellular death mechanism induced by this peptide in cells of Crohn's disease patients. These results are representative of five patients with active Crohn's disease and five healthy donors.

Example 2

Identification of the Cellular Death Mechanism Induced by the APL Peptide in Peripheral Blood Mononuclear Cells from Crohn's Disease Patients by Transmission Electron Microscopy With the objective of identifying if the cellular death mechanism induced by the APL peptide (identified as Seq ID No. 1 in this invention) in peripheral blood mononuclear cells from patients with active Crohn's disease is mediated by apoptosis, the samples were analyzed by transmission electron microscopy (TEM). This technique allows the visualization of the morphological characteristics of apoptotic cells which are an irrefutable criterion of the occurrence of apoptosis. These characteristics are: electron-dense nucleus (perinuclear migration of the chromatin in the early phase), nuclear fragmentation, disorganized and intact cytoplasmic organelles, huge and distinguishable vacuoles, changes in the cellular surface and disintegration of the cell in apoptotic bodies. The process of phagocytosis of the apoptotic bodies by neighboring cells can also be observed with this technique (White M et al. (2004) A morphologic approach to detect apoptosis based on electron microscopy. Methods Mol Biol 285: 105-11).

Mononuclear cells, isolated from peripheral blood ($10\times10^6$ cells) of patients with Crohn's disease, were cultured with and without the APL peptide at a concentration of 40 ug/mL during 72 hours. Untreated cells were used as control of the assay. After 72 hours of incubation, the samples were fixed using a glutaraldehyde solution at 1% and paraformaldehyde at 4% in phosphate buffer 0.1 M during 1 hour. Next, the cells were washed in PBS 1× and were treated with a solution of osmium tetraoxide at 2% for 1 h. Later on, cells were washed twice with cocodilate buffer 0.1 M and the samples were dehydrated in growing concentrations of alcohols (30-100%). Subsequently, the cells were infiltrated using an epoxy resin Spurr (Spurr A R (1969) A low-viscosity epoxy resin embedding medium for electron microscopy. J Ultrastruct Head 26(1): 31-43) and the polymerization was carried out at 70° C. for 24 h. The ultrafine sections (40 nm) were cut using an ultramicrotome (Nova, LKB) and were mounted on nickel grills. Later on, the samples were stained with a solution of uranile acetate supersaturated in methanol for 5 minutes. The analysis was carried out in an Electronic Microscope JEOL/JEM 2000 EX (JEOL, Japan).

Figure 2:
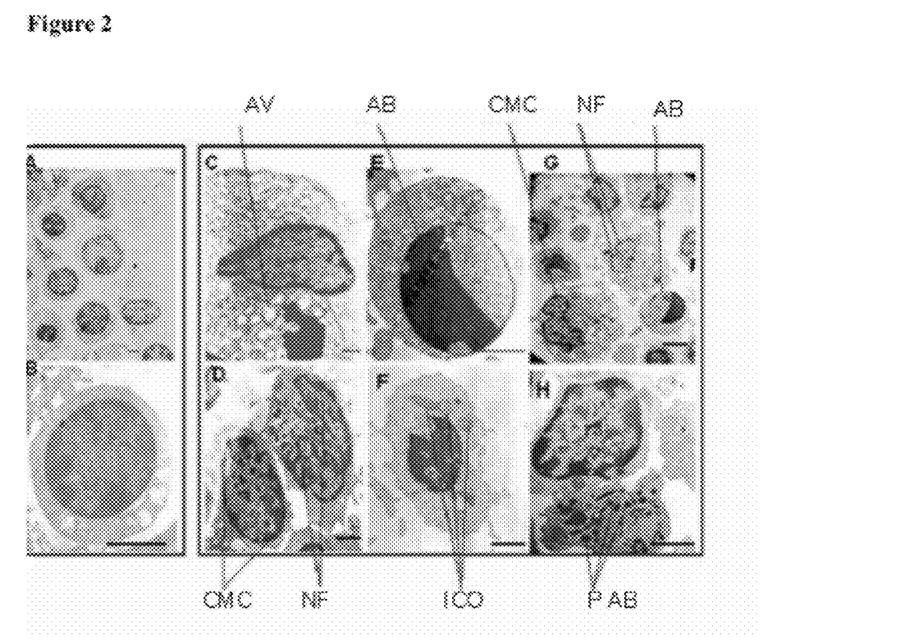
FIGS. 2A-2H. Transmission electron microscopy for the demonstration of apoptosis induced by peptide of Seq ID No. 1 in peripheral blood mononuclear cells from Crohn's disease patients. Panels A, B: Untreated cells (negative control). Panels C-H: Cells treated with peptide of Seq ID No. 1 (40 µg/mL). Abundant Vacuolization (AV); nuclear fragmentation (NF); perinuclear condensation and migration of the chromatin (CMC); intact cytoplasmic organelles (ICO); apoptotic bodies (AB); phagocytosis of the apoptotic bodies (P AB).
Figure 3:
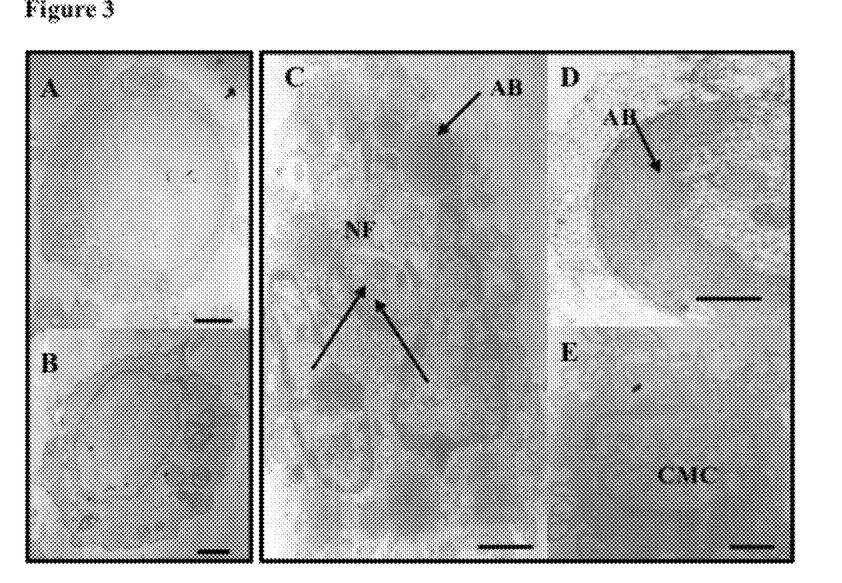
FIGS. 3A-3E. Transmission electron microscopy for demonstration of apoptosis induced by peptide of Seq ID No. 1 in mononuclear cells from intestinal lamina propria of Crohn's disease patients. Panels A, B: Untreated cells (negative control). Panels C, D, E: Cells treated with peptide of Seq ID No. 1 (40 µg/mL). Nuclear fragmentation (NF); perinuclear condensation and migration of the chromatin (CMC); apoptotic body (AB).

In FIG. 2 are shown the results obtained by TEM in mononuclear cells from patients with active Crohn's disease. As it is observed, untreated cells have a normal morphology (A, B). However, in cells treated with the APL peptide (Seq ID No. 1) the morphological changes characteristic of an apoptotic process can be observed (C-H). In particular, it can be observed the condensation and migration of the chromatin to the periphery of the nucleus (CMC), which is one of the earliest morphological changes that take place during the apoptosis in the nucleus (N) of cells. Also, nuclear fragmentation (NF) and apoptotic bodies (AB) were observed in these samples. Even, by the presence of cellular debris can be known that the phagocytosis of the apoptotic bodies (P AB) occurred. Cytoplasmic organelles remain intact (ICO) as observed in the FIG. 2F, which is a characteristic of the cellular death by apoptosis. These results demonstrate that the cellular death mechanism induced by this APL peptide in mononuclear cells from patients with active Crohn's disease is mediated by apoptosis.

The analysis of these patient cells performed by TEM also allowed the identification of the cell population among the mononuclear cells that fall into apoptosis. This result was possible because the different types of leukocytes of the blood (monocytes, lymphocytes and polymorfonuclears) have different morphologies.

Among mononuclear cells, we identified that lymphocytes are the population that falls into apoptosis. From a morphological point of view, lymphocytes are smaller than monocytes, also have a round nucleus and less cytoplasm. Furthermore, lymphocytes do not present nucleus with lax chromatin or with a horseshoe form, which is characteristic of monocytes (Junqueira L C and Carneiro J (2005) Basic Histology. Sixth edition. Editorial Masson, Barcelona, Spain).

Example 3

Identification of the Cellular Death Mechanism Induced by the APL Peptide on Intestinal Lamina Propria Mononuclear Cells from Crohn's Disease Patients Samples from intestinal tissues corresponding to inflamed patches were obtained with written consent. Samples were maintained in cold, magnesium and calcium free Hank's balanced salt solution (HBSS). Lamina propria mononuclear cells were isolated from these tissues using the Dithiothreitol/Ethylenediamine tetraacetic acid/Collagenase method described by Bull and Bookman (Bull D M K and Bookman M A (1977) Isolation and functional characterization of human intestinal mucosal lymphoid cells. J Clin Invest 59: 966-974) with the modifications carried out by Van Tol and colleagues (Van Tol E A et al. (1992) The CD56 adhesion molecule is the major determinant for detecting non-major histocompatibility complex-restricted cytotoxic mononuclear cells from the intestinal lamina propria. Eur J Immunol 22: 23-29).

Lamina propria mononuclear cells from Crohn's disease patients ($10 \times 10^6$ cells) were cultured with and without APL peptide (Seq ID No. 1) (40 ug/mL) during 72 hours. The analysis carry out by TEM (FIG. 3) revealed that this peptide induces the death by apoptosis of a great part of this population, as can be observed in cells treated with the APL peptide some of the morphological characteristics of this type of cellular death (C-E) such as: the migration of the chromatin to the periphery of the nucleus (CMC), nuclear fragmentation (NF) and apoptotic bodies (AB). Untreated cells have a normal morphology (A-B).

Example 4

Decrease in the Viability of Peripheral Blood Mononuclear Cells from Patient with Inactive Crohn's Disease after being Activated with an Anti-CD3 Antibody Peripheral blood mononuclear cells from a patient with inactive Crohn's disease were activated with an anti-CD3 antibody (e-Biosciences) during 72 h at 37° C., in humid atmosphere of $CO_2$ at 5%. The addition of the anti-CD3 antibody produces a polyclonal activation of T cells in the cell population. Activated lymphocytes were washed with PBS 1× solution and then incubated ($1 \times 10^5$ cells) for 1 h with different concentrations (10, 40 and 160 ug/mL) of the APL peptide (Seq ID No.1). Peripheral blood mononuclear cells cultured for 72 hours without the anti-CD3 antibody were used as control of the activation assay (non-activated cells). After this time, these cells were cultured with the same concentrations of the APL peptide.

Figure 4:
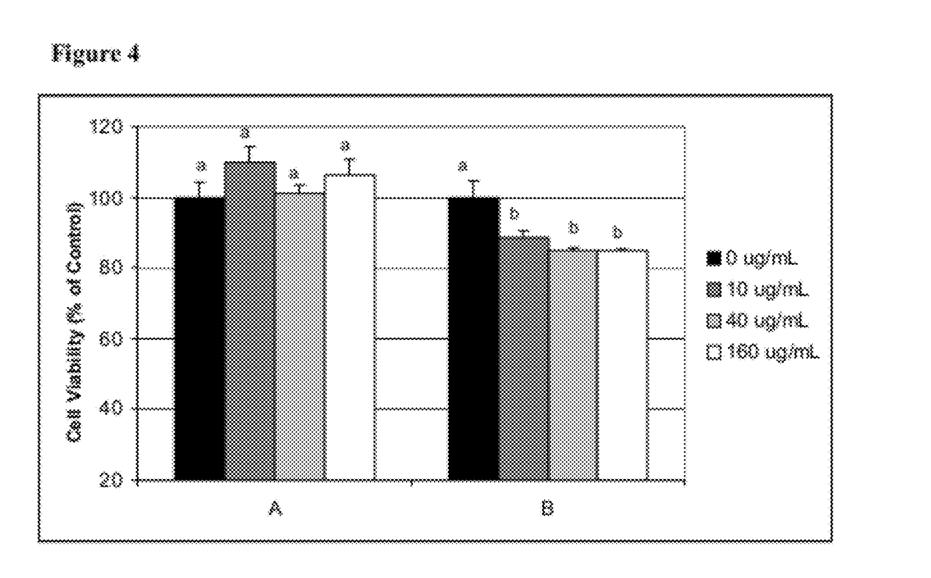
FIGS. 4A-4B. Effect of peptide of Seq ID No. 1 on the viability of mononuclear cells from inactive Crohn's disease patient. In the X axis, A: Non-activated cells with the anti-CD3 antibody, B: Activated cells with the anti-CD3 antibody. Different letters indicate significant statistical differences between the negative control (0 ug/mL) and each one of the doses of the peptide evaluated in this group.

The cellular viability was determined using the MTT method, as described in the Example 1. As it can be observed in FIG. 4A, the APL peptide does not reduce the viability of mononuclear cells from a patient with inactive Crohn's disease. However, this peptide significantly reduced the viability of these cells previously activated with the anti-CD3 antibody (B). This result, together with those that are shown in Examples 1 and 2, in which this peptide does not affect the viability of mononuclear cells from healthy donors (Example 1) and the identification of lymphocytes as the major population of mononuclear cells from patients with active Crohn's disease that falls into apoptosis (Example 2), suggest that this APL peptide (Seq ID No.1) is able to induce the apoptosis of pathogenic activated T cells with high specificity.

Example 5

Evaluation of the Effect of the APL Peptide on the Viability of Peripheral Blood Mononuclear Cells from Patients with Diabetes Mellitus Type 1

Figure 5:
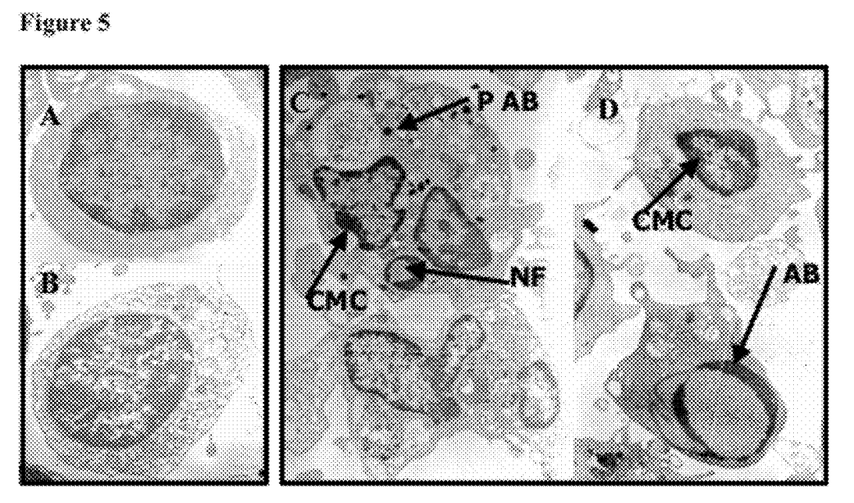
FIG. 5A-5D. Transmission electron microscopy for demonstration of apoptosis induced by peptide of Seq ID No. 1 in peripheral blood mononuclear cells from diabetes mellitus type 1 patients. Panels A, B: Untreated cells (negative control). Panels C-D: Cells treated with peptide of Seq ID No. 1 (40 µg/mL). Nuclear fragmentation (NF); perinuclear condensation and migration of the chromatin (CMC); apoptotic body (AB); phagocytosis of the apoptotic bodies (P AB).
Figure 6:
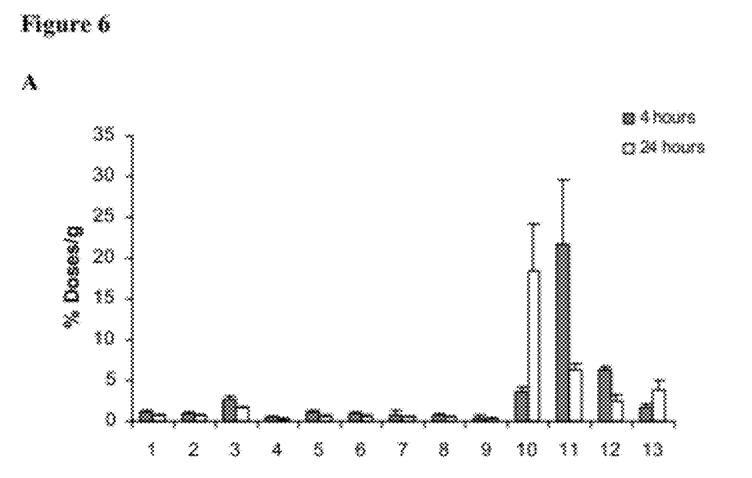
FIGS. 6A-6D. Biodistribution study of the peptide of Seq ID No. 1 in Lewis rats. A: intravenous route 0.25 mg/kg body weight. B: intravenous route 1 mg/kg body weight. C: intradermal route 0.25 mg/kg body weight. D: intradermal route 1 mg/kg body weight. The analyzed tissues are: 1. Liver; 2. Spleen; 3. Kidneys; 4. Heart; 5. Lungs; 6. Cervical ganglion; 7. Axillary-brachial ganglion; 8. Mesenteric ganglion chain; 9. Pelvic ganglion; 10. Thyroid; 11. Stomach; 12. Small intestine; 13. Large intestine.

Peripheral blood mononuclear cells from patients with diabetes mellitus type 1 were isolated by centrifugation over Ficoll-Paque™ PLUS, a density gradient medium for the isolation of mononuclear cells, as it is described in Example 1. To do that, $10 \times 10^6$ cells were treated with the APL peptide (40 ug/mL) during 72 hours. Untreated cells were used as control of the assay. As it is shown in FIG. 5, cells treated with this peptide have the previously described morphology (in the Example 2) of the cells on apoptosis (Panels C-D). On the other hand, untreated cells (Panels A-B) have a normal morphology. This result demonstrates that this APL peptide induces apoptosis in mononuclear cells from patients with diabetes mellitus type 1.

Example 6

Biodistribution Study of the APL Peptide (Identified as Seq Id No. 1) in Lewis Rats The APL peptide (identified as Seq ID No. 1) was labeled with $I^{125}$ isotope and it was administered to Lewis rats at doses of 0.25 mg and 1 mg/Kg body weight, by intravenous and intradermal route. Six animals were sacrificed from each experimental group, at 4 and 24 h after peptide inoculation. Radioactivity levels were determined in different organs. Results are expressed on % of radioactivity dose/g of tissue.

This study indicated that this peptide is biodistributed into the gastrointestinal tract: stomach, small intestine and colon, remaining in these organs the necessary time to exert its biological mechanisms. This result endorses the use of this peptide for the treatment of the inflammatory bowel diseases, as Crohn's disease and ulcerative colitis. Furthermore, this peptide can be applied for the treatment of other autoimmune diseases like diabetes mellitus type 1, because the gastrointestinal tract is the site of excellence for induction of peripheral tolerance.

The invention claimed is:

1. A method of inducing apoptosis of pathogenic clones of T cells in patients with inflammatory bowel disease and type 1 Diabetes, said method comprising administering an effective amount of a pharmaceutical composition comprising an Altered Peptide Ligand (APL) peptide identified as SEQ ID NO: 1.

2. The method according to claim 1, wherein the inflammatory bowel disease is selected from the group that comprises Crohn's disease and ulcerative colitis.

3. The method according to claim 1, wherein the pharmaceutical composition is administered by parenteral or mucosal route.

4. The method according to claim 3, wherein the pharmaceutical composition is administered by a parenteral route selected from the group that comprises the intradermal route, the subcutaneous route, the intramuscular route and the intravenous route.

5. The method according to claim 3, wherein the pharmaceutical composition is administered by a mucosal route selected from the group that comprises the rectal route and the oral route.

* * * * *

UNITED STATES PATENT AND TRADEMARK OFFICE
CERTIFICATE OF CORRECTION

PATENT NO. : 8,410,057 B2
APPLICATION NO. : 13/142471
DATED : April 2, 2013
INVENTOR(S) : Barbera Betancourt et al.

It is certified that error appears in the above-identified patent and that said Letters Patent is hereby corrected as shown below:

IN THE PATENT:

Column 1, line 34
Now reads: "lead to the chronic activation of these lymphocytes remain";
Should read: -- leads to the chronic activation of these lymphocytes remains --.

Column 3, line 31
Now reads: "effects as it been suggested";
Should read: -- effects as it has been suggested --.

Column 3, line 59
Now reads: "by to dual altered peptide";
Should read: -- by a dual altered peptide --.

Column 9, line 49
Now reads: "analysis carry out by TEM";
Should read: -- analysis carried out by TEM --.

Column 10, line 5
Now reads: "(10, 40 and 160 ug/mL)";
Should read: -- (10, 40 and 160 µg/mL) --.

Column 10, line 37
Now reads: "(40 ug/mL)";
Should read: -- 40 µg/mL) --.

Signed and Sealed this
Fifth Day of November, 2013

Teresa Stanek Rea
*Deputy Director of the United States Patent and Trademark Office*